United States Patent [19]

Debono

[11] Patent Number: 4,604,380

[45] Date of Patent: Aug. 5, 1986

[54] C-23-SUBSTITUTED MYCAMINOSYLTYLONOLIDE COMPOUNDS, PHARMACEUTICAL COMPOSITIONS AND METHODS OF USE

[75] Inventor: Manuel Debono, Indianapolis, Ind.

[73] Assignee: Eli Lilly and Company, Indianapolis, Ind.

[21] Appl. No.: 692,484

[22] Filed: Jan. 18, 1985

[51] Int. Cl.$^4$ .................. A61K 31/71; C07H 17/08
[52] U.S. Cl. ........................... 514/30; 536/7.1
[58] Field of Search ................. 536/7.1; 514/30

[56] References Cited

U.S. PATENT DOCUMENTS

| | | | |
|---|---|---|---|
| 4,436,729 | 3/1984 | Ganguly et al. | 424/180 |
| 4,438,109 | 3/1984 | Umezawa et al. | 424/180 |
| 4,454,314 | 6/1984 | Nagel | 536/7.1 |
| 4,459,290 | 7/1984 | Kirst et al. | 424/180 |
| 4,463,171 | 7/1984 | Umezawa et al. | 424/180 |
| 4,468,511 | 8/1984 | Kirst et al. | 536/7.1 |
| 4,477,443 | 10/1984 | Umezawa et al. | 424/180 |
| 4,490,524 | 12/1984 | Fujiwara et al. | 536/7.1 |

OTHER PUBLICATIONS

A. Tanaka et al., "Synthesis of 23-Dialkylamino Derivatives of Mycaminosyl Tylonolide and 4'-Deoxymycaminosyl Tylonolide Effective Against Gram-Negative Bacteria", *J. Antibiotics*, 35 (1) 113-116 (1982).

S. Sakamoto et al., "Synthesis of 23-Deoxy-23-N-ethyl-23-(2-fluoro-, 2,2-difluoro-, and 2,2,2-trifluoroethyl)amino Derivatives of Mycaminosyl Tylonolide and 4'-Deoxymycaminosyl Tylonolide", *J. Antibiotics*, 37 (12), 1628–1634 (1984).

M. Debono et al., copending U.S. application Ser. No. 614,343, filed May 25, 1984 entitled "C-20- and C-2-3-Modified Macrolide Derivatives", which is a continuation-in-part of application Ser. No. 470,833, filed Feb. 28, 1983.

*Primary Examiner*—Johnnie R. Brown
*Attorney, Agent, or Firm*—Nancy J. Harrison

[57] ABSTRACT

C-23-bicyclic or tricyclic amino derivatives of OMT and 4'-deoxy-OMT, and pharmaceutical compositions comprising and methods of treating infections with these compounds, are provided.

38 Claims, No Drawings

C-23-SUBSTITUTED MYCAMINOSYLTYLONOLIDE COMPOUNDS, PHARMACEUTICAL COMPOSITIONS AND METHODS OF USE

SUMMARY OF THE INVENTION

This invention relates to C-23-substituted macrolide derivatives having formula 1:

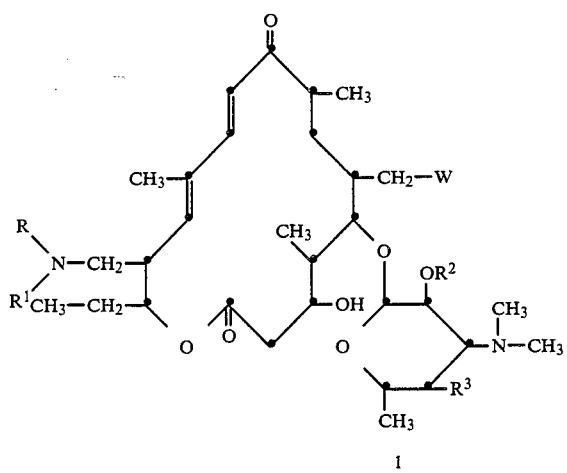

wherein
W represents

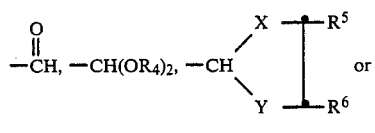

a      b      c

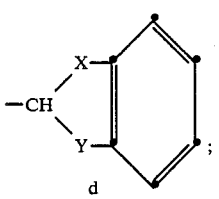

d

R is a bicyclic or tricyclic ring system containing from 6 to 18 carbon atoms; and
$R^1$ is hydrogen, $C_1-C_4$-alkyl or benzyl; or
R and $R^1$ together form a bicyclic or tricyclic ring system containing from 8 to 20 ring atoms wherein one or more of the carbon atoms may be substituted by a group selected from $C_1-C_4$-alkyl, $C_2-C_4$-alkenyl, $C_2-C_4$-alkynyl, $C_1-C_4$-alkoxy, $C_1-C_4$-alkoxycarbonyl, hydroxyl, $C_1-C_4$-alkanoyloxy, $C_1-C_4$-alkanoylamino, halo, halo-$C_1-C_4$-alkyl, $-N(C_1-C_4$-alkyl$)_2$, $-N(CH_2)_m$,

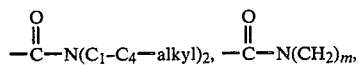

cyano, ethylenedioxy, benzyl, phenyl, or phenyl substituted by from 1 to 3 substituents selected from nitro, halo, $C_1-C_4$-alkyl, $C_1-C_4$-alkoxy, hydroxy, amino, or mono- or di-$(C_1-C_4$-alkyl)amino; and m is an integer from 4 through 7;
$R^2$ is hydrogen, optionally substituted $C_1-C_5$-alkanoyl or optionally substituted benzoyl, phenylacetyl or phenylpropionyl;
$R^3$ is hydrogen or $-OR^2$;
$R^4$ is $C_1-C_4$-alkyl;
$R^5$ and $R^6$, independently, are hydrogen, methyl, ethyl, phenyl, methoxycarbonyl, ethoxycarbonyl or phenoxycarbonyl;
X and Y, independently, represent O, S or $NR^7$; and
$R^7$ is hydrogen, methyl, ethyl, phenyl or benzyl;
and the acid addition salts of these compounds.

Although no stereochemical assignments have been indicated in the figures, the stereochemistry is that of tylosin.

The formula 1 compounds are useful antibiotics or intermediates to antibiotics. This invention also relates to pharmaceutical compositions comprising these compounds and to methods of treatment wherein these compounds or compositions are administered to obtain an antibiotic effect or to enhance growth promotion in animals.

DETAILED DESCRIPTION OF THE INVENTION

This invention relates to new antibiotics. In particular, this invention relates to a group of C-23-modified derivatives of the macrolide antibiotics 5-O-mycaminosyltylonlide (OMT) and 4'-deoxy-OMT and to the acid addition salts of these derivatives. This invention also relates to methods of treating certain infections with, methods of promoting growth in animals with, and pharmaceutical compositions comprising the specified derivatives and their pharmaceutically acceptable acid addition salts.

New, improved antibiotics continue to be in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer in vivo half life, and more advantageous rate or route of excretion and rate or pattern of metabolism) are some of the goals for improved antibiotics.

OMT is an antibiotic described by M. Gorman and R. B. Morin in U.S. Pat. No. 3,459,853, issued on Aug. 5, 1969. The 4'-deoxy derivative of OMT is prepared from OMT as described by Tanaka et al. in J. Antibiotics 34 (10), 1374–1376 (1981). The structures of OMT and 4'-deoxy-OMT are shown in formulas 2 and 3, respectively:

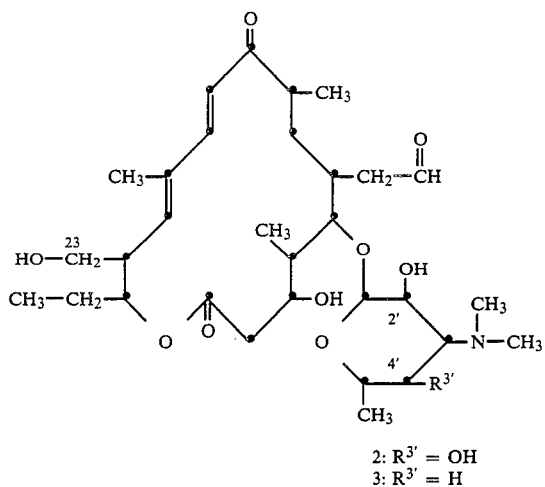

2: $R^{3'}$ = OH
3: $R^{3'}$ = H

Certain derivatives of this invention, i.e. the formula 1a compounds and their acid addition salts, have excellent antibacterial activity, as measured by minimal inhibitory concentration (MIC) values against representative bacteria and Mycoplasma species. The formula 1b, 1c and 1d compounds and their acid addition salts also have antibacterial activity and are useful as intermediates to the formula 1a compounds.

Representative R groups are bicycloheptyl, bicyclooctyl and tricyclodecyl. Norbonyl (or bicyclo[2.2.1]heptyl) is an example of a bicycloheptyl group; bicyclo[3.2.1]octyl is an example of a bicyclooctyl group; and adamantyl (or tricyclo[3.3.1.1$^{3,7}$]decyl) is an example of a tricyclodecyl group.

Representative groups when R an $R^1$ together form a bicyclic or tricyclic ring system are 1,2,3,4-tetrahydroquinolin-1-yl; 1,2,3,4-tetrahydroisoquinolin-2-yl; indol-1-yl; octahydroindol-1-yl; 1,3,3a,4,7,7a-hexahydro-2H-isoindol-2-yl; indolin-1-yl; octahydroisoindol-1-yl; isoindolin-2-yl; 2,3,4,5-tetrahydro-1H-1-benzazepin-1-yl; 2,3,4,5-tetrahydro-1H-2-benzazepin-2-yl; 2,3,4,5-tetrahydro-1H-3-benzazepin-3-yl; carbazol-9-yl; 9,10-dihydroacridin-10-yl; octahydrocyclopenta[b]pyrrol-1-yl; decahydroquinolin-1-yl; decahydroisoquinolin-2-yl; decahydrocyclohepta[b]pyrrol-1-yl; decahydrocyclohepta[c]pyrrol-2-yl; decahydrocyclopent[c]azepin-2-yl; decahydrocyclopent[d]azepin-3-yl; 5,6-dihydrophenanthridin-5-yl; an azabicycloheptanyl group such as 3-azabicyclo[3.2.0]heptan-3-yl; an azibicyclooctanyl group such as 6-azabicyclo[3.2.1]octan-6-yl; an azibicyclononanyl group such as 3-azabicyclo[3.2.2]nonan-3-yl; an azabicyclodecanyl group such as 4-azabicyclo[5.3.0]decan-4-yl; an azatricyclogroup such as 2-azatricyclo[6.2.2.2$^{3,6}$]tetradecan-2-yl or dodecahydrocarbazol-9-yl; and a spiro-fused system such as 1-azaspiro[4.5]decan-1-yl or 3-azaspiro[5.5]undecan-3-yl.

Representative groups when R has one or more substituents on the carbon atoms of the ring system include 1,3,3-trimethyl-6-azabicyclo[3.2.1]octan-6-yl; 4-methyl-2-azabicyclo[4.2.0]octan-2-yl; and 5,7-dimethyl-1-azaspiro[2.5]octan-1-yl.

The terms "$C_1$-$C_4$-alkyl", "$C_1$-$C_4$-alkoxy" and "$C_1$-$C_4$ $_{or}$ 5-alkanoyl" as used herein mean a moiety containing one of the specified numbers of carbon atoms. Unless otherwise specified, the alkyl group in such a moiety can be straight, branched, or cyclic. When optionally substituted, the group can bear one to three halo substituents. Halo substituents are selected from the group consisting of Cl, Br and F. Exemplary $C_1$-$C_4$-alkyl groups include methyl, ethyl, isopropyl, cyclopropyl, n-butyl, sec-butyl, isobutyl and tert-butyl. Methoxy, ethoxy and propoxy are typical $C_1$-$C_4$-alkoxy groups. Examples of $C_1$-$C_4$ $_{or}$ 5-alkanoyl groups are acetyl, chloroacetyl, trichloroacetyl, trifluoroacetyl, propionyl, n-butyryl, isobutyryl, n-valeryl, and isovaleryl.

The term —N(CH$_2$)$_m$ refers to a monocyclic amino group containing the specified number of carbon atoms. Pyrrolidin-1-yl, piperidin-1-yl, and octahydro-1H-azocin-1-yl are examples of such groups.

The term "optionally substituted benzoyl, phenylacetyl or phenylpropionyl" means that the phenyl portion of the moiety can bear from one to five halo or methyl or from one to two methoxyl, nitro or hydroxyl groups.

The formula 1 compounds can be prepared from OMT and 4'-deoxy-OMT by conventional displacement methods (see, for example, U.S. Pat. No. 4,459,290). Displacement is accomplished in three steps. In the first step, the C-23-hydroxyl group is converted to a suitable leaving group, such as an iodo group. In the second step, the aldehyde function at C-20 is protected by converting it to a ketal intermediate, using well-known methods (see, for example, T. W. Greene, "Protective Groups in Organic Synthesis," John Wiley and Sons, New York, 1981, p. 116–140).

In the third step, the leaving group is displaced with the appropriate amine, using standard conditions, to give a formula 1b, 1c or 1d compound. Formula 1a compounds are prepared by hydrolysis of a 1b, 1c, or 1d intermediate.

The formula 1 derivatives wherein $R^2$ is other than hydrogen (ester derivatives) may be prepared by treating the corresponding C-23-substituted derivative wherein $R^2$ is hydrogen with acylating agents, using standard methods exemplified in the art (See, for example U.S. Pat. No. 4,401,660).

The formula 1 derivatives of this invention form acid addition salts. These acid addition salts are also useful as antibiotics or as intermediates to antibiotics and are a part of this invention. Salts are useful as intermediates, for example, for separating and purifying the formula 1 compounds. In addition, salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthaic, tartaric, formic, lauric, stearic, salicylic, methanesulfonic, benzenesulfonic, sorbic, picric, benzoic, cinnamic, and like acids.

Pharmaceutically acceptable acid addition salts are an advantageous group of salts of this invention.

Because of their excellent activity, the formula 1a compounds are preferred compounds of this invention. Formula 1a compounds wherein R and $R^1$ together form a bicyclic or tricyclic ring system are especially preferred.

Those compounds wherein R and $R^1$ form a decahydroquinolinyl; decahydroisoquinolinyl; tetrahydroquinolinyl; tetrahydroisoquinolinyl; 3-azabicyclo[3.2.1]nonanyl; 6-azabicyclo[3.2.1]octanyl; 3-azaspiro[5.5]undecanyl; 1-azaspiro[4.5]decanyl; octahydroindolyl, octahydroisoindolyl; hexahydroisoindolyl; or dihydroindolyl group are especially preferred. When R is a bicyclic or tricyclic ring system, a preferred R group is adamantyl.

Illustrative formula 1 compounds of this invention are listed in Tables I and II.

TABLE I

Illustrative Cycloalkylamino Derivatives of Formula 1

| Compound No. | W | —R | $R^1$ | $R^2$ | $R^3$ |
|---|---|---|---|---|---|
| 1 | O=CH— | 1-adamantyl | H | H | —OH |
| 2 | " | " | $CH_3$ | H | —OH |
| 3 | " | " | t-butyl | H | —OH |
| 4 | " | " | H | H | H |
| 5 | " | " | H | Ac | —OH |
| 6 | " | bicyclo[2.2.1]-hept-2-yl | benzyl | H | —OH |
| 7 | " | bicyclo[2.2.1]-hept-2-yl | H | H | —OH |
| 8 | " | bicyclo[2.2.1]-hept-2-yl | n-propyl | H | —OH |
| 9 | —CH(OEt)$_2$ | 1-adamantyl | H | H | —OH |
| 10 | " | " | $CH_3$ | H | —OH |
| 11 | " | " | t-butyl | H | —OH |
| 12 | " | " | H | H | H |
| 13 | " | " | H | Ac | —OH |
| 14 | " | bicyclo[2.2.1]-hept-2-yl | benzyl | H | —OH |
| 15 | " | bicyclo[2.2.1]-hept-2-yl | H | H | —OH |
| 16 | " | bicyclo[2.2.1]-hept-2-yl | n-propyl | H | —OH |

TABLE II

Illustrative Cycloamino Derivatives of Formula 1

| Compound No. | W | —N(RR$^1$) Group | $R^2$ | $R^3$ |
|---|---|---|---|---|
| 17 | O=CH— | 3-azabicyclo[3.2.2]non-3-yl | H | —OH |
| 18 | " | " | H | —H |
| 19 | " | " | Ac | acetoxy |
| 20 | " | decahydroquinolin-1-yl | H | —OH |
| 21 | " | " | Ac | acetoxy |
| 22 | " | " | Ac | H |
| 23 | " | 1,3,3-trimethyl-6-azabicyclo-[3.2.1]oct-6-yl | H | —OH |
| 24 | " | 1,3,3-trimethyl-6-azabicyclo-[3.2.1]oct-6-yl | H | H |
| 25 | " | dodecahydro-9H—carbazol-9-yl | H | —OH |
| 26 | " | dodecahydro-9H—carbazol-9-yl | H | H |
| 27 | " | 3-azaspiro[5.5]undec-3-yl | H | —OH |
| 28 | " | " | H | H |
| 29 | " | 3,4-dihydro-1H—isoquinolin-2-yl | H | —OH |
| 30 | " | 3,4-dihydro-1H—isoquinolin-2-yl | Ac | acetoxy |
| 31 | " | 1-azaspiro[4.5]dec-1-yl | H | —OH |
| 32 | " | " | H | H |
| 33 | " | octahydro-1H—isoquinolin-2-yl | H | —OH |
| 34 | " | octahydro-1H—isoquinolin-2-yl | H | H |
| 35 | " | octahydro-1H—indol-1-yl | H | —OH |
| 36 | " | " | Ac | acetoxy |
| 37 | " | 1,2,3,3a,4,7,7a-hexahydro-2H—isoindol-2-yl | H | —OH |
| 38 | " | 1,2,3,3a,4,7,7a-hexahydro-2H—isoindol-2-yl | H | H |
| 39 | —CH(OEt)$_2$ | 3-azabicyclo[3.2.2]non-3-yl | H | —OH |
| 40 | " | " | H | —H |
| 41 | " | " | Ac | acetoxy |
| 42 | " | decahydroquinolin-1-yl | H | —OH |
| 43 | " | " | Ac | acetoxy |
| 44 | " | " | Ac | H |
| 45 | " | 1,3,3-trimethyl-6-azabicyclo-[3.2.1]oct-6-yl | H | —OH |
| 46 | " | 1,3,3-trimethyl-6-azabicyclo-[3.2.1]oct-6-yl | H | H |
| 47 | " | dodecahydro-9H—carbazol-9-yl | H | —OH |
| 48 | " | dodecahydro-9H—carbazol-9-yl | H | H |
| 49 | " | 3-azaspiro[5.5]undec-3-yl | H | —OH |
| 50 | " | " | H | H |
| 51 | " | 3,4-dihydro-1H—isoquinolin-2-yl | H | —OH |
| 52 | " | 3,4-dihydro-1H—isoquinolin-2-yl | Ac | acetoxy |
| 53 | " | 1-azaspiro[4.5]dec-1-yl | H | —OH |
| 54 | " | " | H | H |
| 55 | " | octahydro-1H—isoquinolin-2-yl | H | —OH |
| 56 | " | octahydro-1H—isoquinolin-2-yl | H | H |
| 57 | " | octahydro-1H—indol-1-yl | H | —OH |
| 58 | " | " | Ac | acetoxy |
| 59 | " | 1,2,3,3a,4,7,7a-hexahydro-2H—isoindol-2-yl | H | —OH |
| 60 | " | 1,2,3,3a,4,7,7a-hexahydro-2H—isoindol-2-yl | H | H |

The formula 1a compounds of this invention inhibit the growth of pathogenic bacteria, both Gram-positive and Gram-negative, and Mycoplasma species. For example, Tables III and IV show the MIC's at which illustrative compounds of this invention inhibit certain organisms. The MIC's s in Table III were determined by standard agar-dilution assays. The MIC's in Table IV were obtained using a conventional broth-dilution microtiter test.

TABLE III

Antibiotic Activity of Formula 1a Compounds[a]

| Test Organism | 1 | 6 | 17 | 20 | 23 | 25 | 27 | 29 | 31 | 33 | 35 | 37 |
|---|---|---|---|---|---|---|---|---|---|---|---|---|
| *Staphylococcus aureus* X1.1 | 0.5 | 0.25 | 0.5 | 0.25 | 0.5 | 0.5 | 0.5 | 0.25 | 0.5 | 0.5 | 0.25 | 0.25 |
| *Staphylococcus aureus* V41[c] | 0.5 | 0.25 | 0.5 | 0.25 | 0.5 | 0.5 | 0.5 | 0.25 | 0.5 | 0.5 | 0.25 | 0.25 |
| *Staphylococcus aureus* X400[d] | 0.5 | 0.25 | 0.5 | 0.5 | 0.5 | 1 | 0.5 | 0.25 | 0.5 | 0.25 | 0.25 | 0.25 |
| *Staphylococcus aureus* S13E | 0.5 | 0.25 | 0.5 | 0.25 | 0.5 | 0.5 | 0.5 | 0.25 | 0.5 | 0.5 | 0.25 | 0.25 |
| *Staphylococcus epidermidis* EPI1 | 0.5 | 0.25 | 0.5 | 0.25 | 0.5 | 0.5 | 0.5 | 0.125 | 0.5 | 0.5 | 0.25 | 0.25 |
| *Staphylococcus epidermidis* 222 | 0.125 | 0.06 | 0.25 | 0.125 | 0.125 | 0.25 | 0.25 | 0.125 | 0.25 | 0.125 | 0.125 | 0.06 |
| *Streptococcus pyogenes* C203 | 0.125 | 0.06 | 0.25 | 0.125 | 0.25 | 0.25 | 0.25 | 0.06 | 0.125 | 0.03 | 0.5 | 0.06 |
| *Streptococcus pneumoniae* Park I | 0.06 | 0.125 | 0.06 | 0.03 | 0.06 | 0.125 | 0.06 | 0.03 | 0.03 | 0.06 | 1 | 0.125 |
| Streptococcus Group D X66 | 0.5 | 0.25 | 0.5 | 0.5 | 0.5 | 0.5 | 0.25 | 0.125 | 0.25 | 0.5 | 0.25 | 0.125 |
| Streptococcus Group D 2041 | 0.5 | 0.25 | 1 | 0.25 | 0.5 | 0.5 | 0.5 | 0.25 | 0.25 | 0.5 | 0.25 | 0.25 |

TABLE III-continued

Antibiotic Activity of Formula 1a Compounds[a]

| Test Organism | Test Compound[b] | | | | | | | | | | | |
|---|---|---|---|---|---|---|---|---|---|---|---|---|
| | 1 | 6 | 17 | 20 | 23 | 25 | 27 | 29 | 31 | 33 | 35 | 37 |
| *Haemophilus influenzae* C.L.[e] | 2 | 1 | 2 | 1 | 2 | 4 | 2 | 1 | 2 | 0.5 | 0.5 | 0.5 |
| *Haemophilus influenzae* 76[f] | 0.5 | 0.5 | 2 | 1 | 1 | 1 | 2 | 1 | 2 | 0.25 | 1 | 1 |

[a]Activity = MIC in mcg/mL
[b]Compound numbers from Tables I and II
[c]Penicillin-resistant strain
[d]Methicillin-resistant strain
[e]Ampicillin-sensitive strain
[f]Ampicillin-resistant strain

TABLE IV

Antibiotic Activity of Formula 1a Compounds[a]

| Test Organism | Test Compound[b] | | | | | |
|---|---|---|---|---|---|---|
| | 1 | 17 | 20 | 23 | 25 | 31 |
| *Staphylococcus aureus* 19C | 0.78 | 0.78 | 1.56 | 1.56 | 0.78 | 0.39 |
| Streptococcus sp. 19F | <0.048 | 0.39 | <0.048 | <0.048 | <0.048 | <0.048 |
| *Pasteurella multocida* 17E[c] | 0.78 | 0.78 | 0.78 | 0.78 | 1.56 | 0.39 |
| *Pasteurella multocida* 60A[d] | 0.78 | 0.78 | 0.78 | 1.56 | 1.56 | 0.39 |
| *Pasteurella multocida* 40G | 0.78 | 0.39 | 0.39 | 0.78 | 1.56 | 0.195 |
| *Pasteurella multocida* 22A | 0.78 | 0.39 | 0.78 | 0.39 | 1.56 | 0.39 |
| *Pasteurella multocida* 68C | 0.78 | 0.39 | 0.78 | 0.78 | 1.56 | 0.39 |
| *Pasteurella hemolytica* 23C | 1.56 | 0.39 | 0.78 | 1.56 | 1.56 | 0.39 |
| *Pasteurella hemolytica* 41D | 1.56 | 0.39 | 1.56 | 1.56 | 1.56 | 0.39 |
| *Pasteurella hemolytica* 22C | 3.12 | 0.39 | 3.12 | 1.56 | 3.12 | 0.78 |
| *Bordetella bronchisepticum* 95B | 6.25 | 6.25 | 6.25 | 12.5 | 25 | 6.25 |
| *Mycoplasma gallisepticum* 29C | 0.097 | <0.048 | >0.048 | <0.048 | 0.097 | 0.097 |
| *Mycoplasma gallisepticum* 15E | 6.25 | 50 | 0.39 | NT[e] | 50 | 50 |
| *Mycoplasma gallisepticum* 36H | 6.25 | 50 | 0.78 | 3.12 | 50 | 50 |
| *Mycoplasma synoviae* 40A | <0.048 | <0.048 | <0.048 | <0.048 | <0.048 | 0.195 |
| *Mycoplasma hyorhinis* 29E | 0.39 | 0.39 | 0.39 | 1.56 | <0.048 | NT |
| *Mycoplasma hyopneumoniae* S5972 | <0.024 | 0.048 | <0.024 | 0.048 | <0.012 | 0.097 |

[a]Activity = MIC in mcg/mL
[b]Compound numbers from Tables I and II
[c]Bovine isolate
[d]Avian isolate
[e]NT = not tested Certain formula 1a compounds have also shown in vivo antimicrobial activity against experimental bacterial infections. When two doses of test compound were administered to mice in experimental infections, the activity observed was measured as an $ED_{50}$ value [effective dose in mg/kg to protect 50% of the test animals: see Warren Wick, et al., *J. Bacteriol.* 81, 233–235 (1961)]. $ED_{50}$ values observed are given in Tables V, VI and VII.

TABLE V

$ED_{50}$ Values for Formula 1a Compounds vs. *Staphylococcus aureus* in Mice

| Compound No.[a] | $ED_{50}$ (mg/kg × 2) | |
|---|---|---|
| | Subcutaneous | Oral |
| 1 | 3.58 | |
| 17 | 2.31 | |
| 20 | 10 | |
| 23 | 3.79 | |
| 25 | 7.69 | |
| 27 | 3.08 | |
| 29 | >10 | |
| 31 | 2.15 | |
| 33 | 7.56 | |
| 35 | 3.08, 7.2, 3.24[b] | 100 |
| 37 | 2.74, 3.92, 3.42 | 85 |

[a]Compound numbers from Tables I and II
[b]Results from three tests

TABLE VI

$ED_{50}$ Values for Formula 1a Compounds vs *Streptococcus pyogenes* in Mice

| Compound No.[a] | $ED_{50}$ (mg/kg × 2) | |
|---|---|---|
| | Subcutaneous | Oral |
| 1 | 0.68, 2.23[b] | >100, 81.8 |
| 6 | >10 | >100 |
| 17 | 9.09, >10 | >100 |
| 20 | 0.88, 3.75 | 77 |
| 23 | 2.5, >10 | 100 |
| 25 | 7.43, >10 | 63 |
| 27 | >10 | |
| 29 | >10 | |
| 31 | 7.76, 1.34, 4.62 | 59.5 |
| 33 | >10 | |
| 35 | 1.86, 2.5 | 87.1 |
| 37 | 0.625, 2.04 | 87 |

[a]Compound numbers from Tables I and II
[b]Results from more than one test

TABLE VII

$ED_{50}$ Values for Formula 1a Compounds vs. *Streptococcous pneumoniae* in Mice

| Compound No.[a] | $ED_{50}$ (mg/kg × 2) | |
|---|---|---|
| | Subcutaneous | Oral |
| 1 | 2.5 | |
| 17 | >10 | |
| 20 | 5 | |
| 23 | 3.6 | |
| 25 | >10 | |
| 27 | >10 | |
| 29 | >10 | |
| 31 | 9.22 | |
| 33 | 10 | |
| 35 | 6.73, 3.27, 3.76[b] | 71 |

TABLE VII-continued

ED$_{50}$ Values for Formula 1a Compounds vs. *Streptococcous pneumoniae* in Mice

| Compound No.[a] | ED$_{50}$ (mg/kg × 2) | |
|---|---|---|
| | Subcutaneous | Oral |
| 37 | 1.66, 1.66, 2.97 | 87 |

[a] Compound numbers from Tables I and II
[b] Results from three tests

Table VIII summarizes the results of tests in which illustrative compounds were evaluated against a Pasteurella infection in one-day-old chicks. The compounds were administered parenterally after challenge of the chicks with *Pasteurella multocida* (0.1 mL of a $10^{-4}$ dilution of a twenty-hour tryptose broth culture of an avian *P. multocida* given subcutaneously). In these tests, all non-medicated infected chicks died within 24 hours of Pasteurella challenge. In the tests summarized in Table VIII, the compounds were administered by subcutaneous injection at a dosage of 30 mg/kg, 1 and 4 hours post-challenge of the chicks with *P. multocida*.

TABLE VIII

Activity of Formula 1a Compounds in *Pasteurella multocida*-Infected Chicks

| Test Compound[b] | Number of Deaths/Number Treated |
|---|---|
| 1 | 0/10 |
| 17 | 10/10 |
| 20 | 6/10; 8/10[c] |
| 23 | 10/10; 10/10[c] |
| 31 | 0/10;3/10[c] |

[a] Administered subcutaneously; 30 mg/kg × 2
[b] Compound numbers from Tables I and II
[c] Two tests The invention also relates to methods of controlling bacterial or mycoplasmal infections. In carrying out the methods of this invention, an effective amount of a formula 1 compound is administered to an infected or susceptible warm-blooded animal.

The dose which is effective to control the infection will vary with the severity of the infection and the age, weight, and condition of the animal. The total dose required for protection will generally however, be in the range of from about 1 to about 100 mg/kg and preferably will be in the range of from about 1 to about 50 mg/kg. Suitable dosage regimens can be constructed.

In another aspect, this invention relates to compositions useful for the control of bacterial or mycoplasmal infections. These compositions comprise a formula 1 compound together with a suitable vehicle. Such compositions may be formulated for oral or parenteral administration by methods recognized in the art.

Often the most practical way to administer the compounds is by formulation into the feed supply or drinking water. A variety of feeds, including the common dry feeds, liquid feeds, and pelleted feeds, may be used.

The methods of formulating drugs into animal feeds are well-known. A preferred method is to make a concentrated-drug premix which in turn is used to prepare medicated feeds. Typical premixes may contain from about 1 to about 200 grams of drug per pound of premix. Premixes may be either liquid or solid preparations.

The final formulation of feeds for animals or poultry will depend upon the amount of drug to be administered. The common methods of formulating, mixing, and pelleting feeds may be used to prepare feeds containing a formula 1 compound.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

In order to illustrate this invention, the following examples are provided. Reaction progress is readily followed by TLC on silica gel, using a dichloromethane:methanol:ammonium hydroxide (45:5:0.5) or ethyl acetate:heptane:diethylamine (1:1:0.1) solvent system. Preparative high performance liquid chromatography (HPLC) was conducted on silica gel, using either flash column chromatography or a Waters Prep 500 HPLC unit.

PREPARATION 1

23-Iodo-OMT

OMT (40 g, 67 mmol) was dissolved in dimethylformamide (DMF) (60 mL). Triphenylphosphine (35.2 g, 134 mmol, powder) was then dissolved in this solution with slight heating. This orange solution in a 500-mL 3-neck round-bottom flask was stirred rapidly at ice-bath temperature with a nitrogen atmosphere. Iodine (34 g, 134 mmol, crystals) in DMF (40 ml) was added dropwise to the above solution over a 30-minute period. (A thick yellow slurry forms initially and eventually disappears). The ice bath was removed after I$_2$/DMF addition. The reaction mixture was stirred at room temperature for 2½ hours and then was poured into cold saturated NaHCO$_3$ solution (2 L) and carefully shaken. The product was extracted into CH$_2$Cl$_2$ (2 portions, 1 L total). The CH$_2$Cl$_2$ layer was washed with 0.1M sodium thiosulfate solution (2 L) to remove excess iodine, dried (Na$_2$SO$_4$), filtered and evaporated to give a red-brown oil.

Some of the triphenylphosphine-oxide by-product can be removed at this point by crystallization (in toluene). The remaining material was purified by silica-gel chromatography on a Waters Prep 500 unit to give 28.36 g (60% yield) of 23-iodo-OMT (as a tan foam).

PREPARATION 2

20-Diethylacetal-23-iodo-OMT

23-Iodo-OMT (50.0 g, 70.7 mmol) was dissolved in ethanol (500 mL). 4 A molecular sieves and p-toluenesulfonic acid monohydrate (20.2 g, 106 mmol) were added. The reaction mixture was stirred at room temperature for 1 hour, 15 minutes. Triethylamine (20 mL) was then added, and stirring was continued for another 15 minutes. The reaction mixture was filtered to remove the sieve material, and the filtrate was evaporated to remove the volatiles. The residue was taken up in $CH_2Cl_2$ (600 mL); this was washed with saturated $NaHCO_3$ solution (1 L). The bicarbonate layer was back extracted with $CH_2Cl_2$ (600 mL). The two $CH_2Cl_2$ portions were combined and washed with saturated $NaHCO_3$ solution (250 mL). The $CH_2Cl_2$ layer was separated, dried ($Na_2SO_4$), filtered and evaporated to give 20-diethylacetal-23-iodo-OMT (53 g, 96% yield, tan foam).

EXAMPLE 1

20-Diethylacetal-23-(3-azabicyclo[3.2.2]nonan-3-yl)-OMT (Compound 39)

20-Diethylacetal-23-iodo-OMT (6.2 g, 8 mmol) was dissolved in $CH_3CN$ (60 mL), and 3-azabicyclo[3.2.2]nonane (3.0 g, 24 mmol) was added. The reaction mixture was stirred at reflux temperature for ~2½ hours and then was cooled and filtered. The filtrate was evaporated under vacuum to give a brown foam. This was taken up in $CH_2Cl_2$ and washed with saturated $NaHCO_3$ solution. The $CH_2Cl_2$ was separated, dried ($Na_2SO_4$), filtered, and evaporated under vacuum to give a brown foam. This material was subjected to silica-gel flash chromatography (gradient from $MeOH/CH_2Cl_2$ (1:49) to $MeOH/CH_2Cl_2/NH_4OH$ (12:87.5:0.5) to give 20-diethylacetal-23-(3-azabicyclo[3.2.2]nonan-3-yl)-OMT (light orange foam, 5.2 g, 83.5% yield).

Another method for isolating formula 1 compounds such as compound 39 is to dissolve the crude product in ethyl acetate (following the saturated $NaHCO_3$ wash step) and extract the product into a pH 6.5, 0.5M $NaH_2PO_4$ buffer solution. The buffer solution is made basic with 5N NaOH until the product precipitates. The precipitate is then separated by filtration, dissolved in $CH_2Cl_2$ and washed as described supra with saturated $NaHCO_3$ solution.

A third general method for isolating formula 1 compounds is by crystallization, e.g. from ethyl acetate, ethyl acetate/hexane, $CH_2Cl_2$/petroleum ether or $CH_3CN$.

EXAMPLE 2

23-(3-azabicyclo[3.2.2]nonan-3-yl)-OMT (Compound 17)

20-Diethylacetal-23-(3-azabicyclo[3.2.1]nonan-3-yl)-OMT (4.5 g, 5.8 mmol) was dissolved in $CH_3CN$ (40 mL), and 0.1N HCl (75 mL) was added. The reaction mixture was stirred at room temperature. 1N HCl (10 mL) was added during the initial stages of the reaction after TLC showed it was progressing very slowly. The reaction was complete within 2 hours. The reaction mixture was evaporated under vacuum to remove some of the $CH_3CN$. The acidic aqueous material obtained was neutralized with saturated $NaHCO_3$ solution. The product was extracted with $CH_2Cl_2$. The $CH_2Cl_2$ layer was separated, dried ($Na_2SO_4$), filtered, and evaporated under vacuum to give 23-(3-azabicyclo[3.2.2]nonan-3-yl)-OMT (light orange foam, 3.9 g, 95.5% yield).

Formula 1 compounds such as Compound 17 can also be purified by silica-gel flash chromatography or by the $NaH_2PO_4$ buffer extraction described in Example 1.

EXAMPLES 3-13

The following compounds were prepared, using the procedures described in Example 1:

| Compound No. | Compound | Yield (%) |
|---|---|---|
| 9 | 20-Diethylacetal-23-deoxy-23-(1-adamantylamino)-OMT | 29.2 |
| 14 | 20-Diethylacetal-23-deoxy-23-[N—benzyl-N—(bicyclo[2.2.1]hept-2-yl)-amino]-OMT | 53.8 |
| 42 | 20-Diethylacetal-23-deoxy-23-(decahydroquinolin-1-yl)-OMT | 21.1 |
| 45 | 20-Diethylacetal-23-deoxy-23-(1,3,3-trimethyl-6-azabicyclo[3.2.1]-octan-6-yl)-OMT | 76.9 |
| 47 | 20-Diethylacetal-23-deoxy-23-(dodecahydro-9H—carbazol-9-yl)-OMT | 61.7 |
| 49 | 20-Diethylacetal-23-deoxy-23-(3-azaspiro[5.5]undecan-3-yl)-OMT | 76.9 |
| 51 | 20-Diethylacetal-23-deoxy-23-(3,4-dihydro-1H—isoquinolin-2-yl)-OMT | 69.5 |
| 53 | 20-Diethylacetal-23-deoxy-23-(1-azaspiro[4.5]decan-1-yl)-OMT | 50.0 |
| 55 | 20-Diethylacetal-23-deoxy-23-(octahydro-1H—isoquinolin-2-yl)-OMT | 71.5 |
| 57 | 20-Diethylacetal-23-deoxy-23-(octahydro-1H—indol-1-yl)-OMT | 62.2 |
| 59 | 20-Diethylacetal-23-deoxy-23-(1,3,3a,4,7,7a-hexahydro-2H—isoindol-2-yl)-OMT | 43.7 |

EXAMPLES 14-24

The following compounds were prepared, using the procedures described in Example 2:

| Compound No. | Compound | Yield (%) |
|---|---|---|
| 1 | 23-deoxy-23-(1-adamantanylamino)-OMT | 97.7 |
| 6 | 23-deoxy-23-[N—benzyl-N—(bicyclo[2.2.1]hept-2-yl)amino]-OMT | 72.6 |
| 20 | 23-deoxy-23-(decahydroquinolin-1-yl)-OMT | 83.6 |
| 23 | 23-deoxy-23-(1,3,3-trimethyl-6-azabicyclo[3.2.1]octan-6-yl)-OMT | 91.5 |
| 25 | 23-deoxy-23-(dodecahydro-9H—carbazol-9-yl)-OMT | 88.9 |
| 27 | 23-deoxy-23-(3-azaspiro[5.5]undecan-3-yl)-OMT | 99 |

-continued

| Compound No. | Compound | Yield (%) |
|---|---|---|
| 29 | 23-deoxy-23-(3,4-dihydro-1H—isoquinolin-2-yl)-OMT | 81.7 |
| 31 | 23-deoxy-23-(1-azaspiro[4.5]decan-1-yl)-OMT | 86.4 |
| 33 | 23-deoxy-23-(octahydro-1H—isoquinolin-2-yl)-OMT | 78.5 |
| 35 | 23-deoxy-23-(octahydro-1H—indol-1-yl)-OMT | 74.3 |
| 37 | 23-deoxy-23-(1,3,3a,4,7,7a-hexahydro-2H—isoindol-2-yl-OMT | 98.9 |

EXAMPLES 25-37

The following compounds can be prepared, using the procedures described in Examples 1 or 2:
20-Diethylacetal-23-deoxy-23-[N-(bicyclo[2.2.1]hept-2-yl)amino]-OMT,
20-Diethylacetal-23-deoxy-23-[N-(n-propyl)-N-(bicyclo[2.2.1]hept-2-yl)amino]-OMT,
20-Diethylacetal-4',23-dideoxy-23-(3-azabicyclo[3.2.2]-nonan-3-yl)-OMT,
20-Diethylacetal-4',23-dideoxy-23-(3-azaspiro[5.5]-undecan-3-yl)-OMT,
20-Diethylacetal-4',23-dideoxy-23-(octahydro-1H-isoquinolin-2-yl)-OMT,
20-Diethylacetal-4',23-dideoxy-(dodecahydro-9H-carbazol-9-yl)-OMT,
23-Deoxy-23-[N-(bicyclo[2.2.1]hept-2-yl)amino]-OMT,
23-Deoxy-23-[N-(n-propyl)-N-(bicyclo-[2.2.1]hept-2-yl)amino]-OMT,
4',23-Dideoxy-23-(3-azabicyclo[3.2.2]nonan-3-yl)-OMT,
4',23-Dideoxy-23-(3-azaspiro[5.5]undecan-3-yl)-OMT,
4',23-Dideoxy-23-(octahydro-1H-isoquinolin-2-yl)-OMT, and
4',23-Dideoxy-(dodecahydro-9H-carbazol-9-yl)-OMT.

EXAMPLE 38

Injectable Formulations (A) A formula 1 base is added to propylene glycol. Water and benzyl alcohol are added so that the solution contains 50% (by volume) propylene glycol, 4% (by volume) benzyl alcohol, and 200 mg/ml of a formula 1 base.

(B) A solution is prepared as described in Section A except that the solution contains 50 mg/ml of a formula 1 base.

(C) A solution is prepared as described in Section A except that the solution contains 350 mg/ml of a formula 1 base.

(D) A solution is prepared as described in Section A except that the solution contains 500 mg/ml of a formula 1 tartrate.

(E) A suspension is prepared by adding a finely ground formula 1 compound to carboxymethyl cellulose with thorough mixing so that the suspension contains 200 mg of the formula 1 base per ml of suspension.

I claim:
1. A compound of the formula:

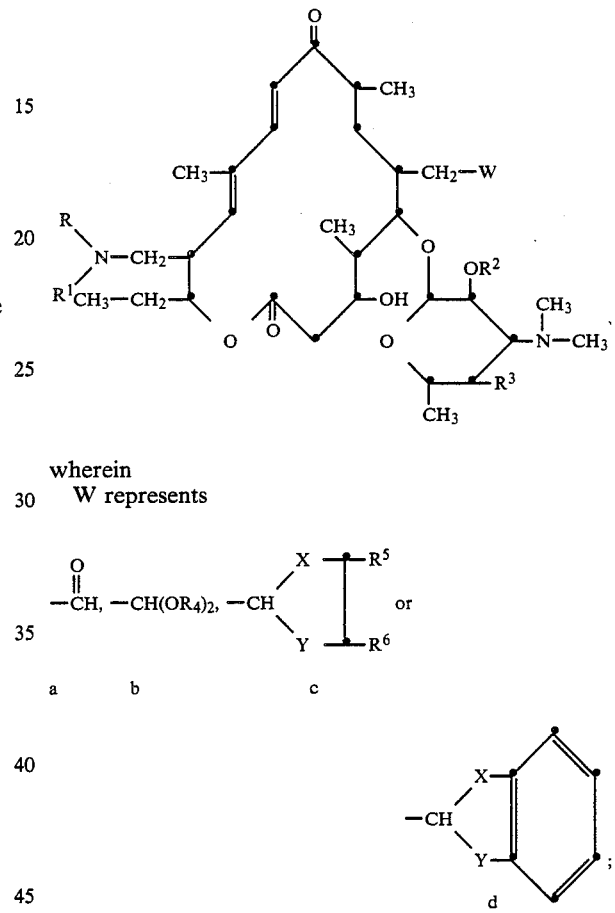

wherein
W represents

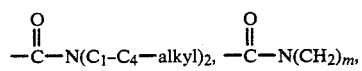

a     b     c $$-CH\begin{matrix}X\\ \diagdown \\ Y\end{matrix}\begin{matrix}\\ \\ \end{matrix};$$

d

R is a bicyclic or tricyclic ring system containing from 6 to 18 carbon atoms; and
$R^1$ is hydrogen, $C_1$–$C_4$-alkyl or benzyl; or
R and $R^1$ together form a bicyclic or tricyclic ring system containing from 8 to 20 ring atoms wherein from 1 to 3 of the carbon atoms may be substituted by a group selected from $C_1$–$C_4$-alkyl, $C_2$–$C_4$-alkenyl, $C_2$–$C_4$-alkynyl, $C_1$–$C_4$-alkoxy, $C_1$–$C_4$-alkoxycarbonyl, hydroxyl, $C_1$–$C_4$-alkanoyloxy, $C_1$–$C_4$-alkanoylamino, halo, halo-$C_1$–$C_4$-alkyl, —N(-$C_1$–$C_4$-alkyl)$_2$, —N(CH$_2$)$_m$, $$-\overset{O}{\underset{\|}{C}}-N(C_1-C_4-\text{alkyl})_2, \quad -\overset{O}{\underset{\|}{C}}-N(CH_2)_m,$$

cyano, ethylenedioxy, benzyl, phenyl, or phenyl substituted by from 1 to 3 substituents selected from nitro, halo, $C_1$–$C_4$-alkyl, $C_1$–$C_4$-alkoxy, hydroxy, amino, or mono- or di-($C_1$–$C_4$-alkyl)amino; and
m is an integer from 4 through 7;

$R^2$ is hydrogen; $C_1$–$C_5$-alkanoyl; $C_1$–$C_5$-alkanoyl having 1 to 3 halo substituents; benzoyl, phenylacetyl or phenylpropionyl; or benzoyl, phenylacetyl or phenylpropionyl having 1 to 5 halo or methyl or 1 to 2 methoxyl, nitro or hydroxyl substituents on the phenyl ring;

$R^3$ is hydrogen or —$OR^2$;

$R^4$ is $C_1$–$C_4$-alkyl;

$R^5$ and $R^6$, independently, are hydrogen, methyl, ethyl, phenyl, methoxycarbonyl, ethoxycarbonyl or phenoxycarbonyl;

X and Y, independently, represent O, S or $NR^7$; and $R^7$ is hydrogen, methyl, ethyl, phenyl or benzyl;

or its acid addition salt.

2. A compound of claim 1 wherein W represents

3. A compound of claim 1 wherein W represents —CH(OR$_4$)$_2$.

4. A compound of claim 1 wherein W represents

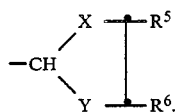

5. A compound of claim 1 wherein W represents

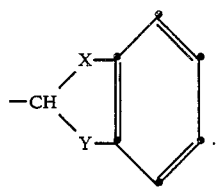

6. A compound of claim 1 wherein R is a tricyclic ring system.

7. A compound of claim 1 wherein R is a bicyclic ring system.

8. A compound of claim 1 wherein R and $R_1$ together form a bicyclic or tricyclic ring system.

9. A compound of claim 6 wherein R is a tricyclodecyl group.

10. A compound of claim 9 wherein R is adamantyl.

11. The compound of claim 10 which is 23-deoxy-23-(1-adamantylamino)-OMT.

12. A compound of claim 7 wherein R is a bicycloheptyl group.

13. A compound of claim 12 wherein R is bicyclo[2.2.1]hept-2-yl.

14. The compound of claim 13 which is 23-deoxy-23-[N-benzyl-N-(bicyclo[2.2.1]hept-2-yl)amino]-OMT.

15. A compound of claim 8 wherein R and $R^1$ form a decahydroquinolinyl group.

16. The compound of claim 15 which is 23-deoxy-23-decahydroquinolin-1-yl-OMT.

17. A compound of claim 8 wherein R and $R^1$ form an octahydroisoquinolinyl group.

18. The compound of claim 17 which is 23-deoxy-23-(octahydro-1H-isoquinolin-2-yl)-OMT.

19. A compound of claim 8 wherein R and $R^1$ form an azabicyclo[3.2.1]octanyl group.

20. The compound of claim 19 which is 23-deoxy-23-(1,3,3-trimethyl-6-azabicyclo[3.2.1]octan-6-yl)-OMT.

21. A compound of claim 8 wherein R and $R^1$ form a dodecahydrocarbazolyl group.

22. The compound of claim 21 which is 23-deoxy-23-(dodecahydro-9H-carbazol-9-yl)-OMT.

23. A compound of claim 8 wherein R and $R^1$ form an azaspiro[5.5]undecanyl group.

24. The compound of claim 23 which is 23-deoxy-23-(3-azaspiro[5.5]undecan-3-yl)-OMT.

25. A compound of claim 8 wherein R and $R^1$ form a dihydroquinolinyl group.

26. The compound of claim 25 which is 23-deoxy-23-(3,4-dihydro-1H-isoquinolin-2-yl)-OMT.

27. A compound of claim 8 wherein R and $R^1$ form an azaspiro[4.5]decanyl group.

28. The compound of claim 27 which is 23-deoxy-23-(1-azaspiro[4.5]decan-1-yl)-OMT.

29. A compound of claim 8 wherein R and $R^1$ form an octahydroindolyl group.

30. The compound of claim 29 which is 23-deoxy-23-(octahydro-1H-indol-1-yl)-OMT.

31. A compound of claim 8 wherein R and $R^1$ form a hexahydroisoindolyl group.

32. The compound of claim 31 which is 23-deoxy-23-(1,3,3a,4,7,7a-hexahydro-2H-isoindol-2-yl)-OMT.

33. A composition useful for the treatment of bacterial or mycoplasmal infections comprising an effective amount of a compound of claim 1 or its pharmaceutically acceptable acid addition salt and a suitable pharmaceutical vehicle.

34. A composition useful for the treatment of bacterial or mycoplasmal infections comprising an effective amount of a compound of claim 2 or its pharmaceutically acceptable acid addition salt and a suitable pharmaceutical vehicle.

35. A composition useful for the treatment of bacterial or mycoplasmal infections comprising an effective amount of a compound of claim 8 or its pharmaceutically acceptable acid addition salt and a suitable pharmaceutical vehicle.

36. A method for treating infections caused by bacterial or mycoplasmal species which comprises administering an effective amount of a composition of claim 33 to an animal.

37. A method for treating infections caused by bacterial or mycoplasmal species which comprises administering an effective amount of a composition of claim 34 to an animal.

38. A method for treating infections caused by bacterial or mycoplasmal species which comprises administering an effective amount of a composition of claim 35 to an animal.

* * * * *